United States Patent
Patterson et al.

(10) Patent No.: US 7,397,556 B2
(45) Date of Patent: Jul. 8, 2008

(54) METHOD, APPARATUS, AND COMPUTER PROGRAM PRODUCT FOR OPTIMIZING INSPECTION RECIPES USING PROGRAMMED DEFECTS

(75) Inventors: Oliver D. Patterson, Poughkeepsie, NY (US); Maryjane Brodsky, Salt Point, NY (US); Kourosh Nafisi, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/554,879

(22) Filed: Oct. 31, 2006

(65) Prior Publication Data

US 2008/0100831 A1    May 1, 2008

(51) Int. Cl.
*G01N 21/00* (2006.01)
*G01R 31/26* (2006.01)
(52) U.S. Cl. .................. 356/237.4; 438/14; 438/16
(58) Field of Classification Search .............. 356/237.4; 438/14, 16
See application file for complete search history.

(56) References Cited

U.S. PATENT DOCUMENTS

| | | | |
|---|---|---|---|
| 5,650,854 A | 7/1997 | Sugawara | |
| 6,048,649 A | 4/2000 | Burke et al. | |
| 7,045,254 B2 | 5/2006 | Dettmann et al. | |
| 2003/0096436 A1* | 5/2003 | Satya et al. | .................... 438/11 |
| 2004/0175633 A1 | 9/2004 | Shoki et al. | |
| 2004/0230883 A1 | 11/2004 | Saito | |

* cited by examiner

*Primary Examiner*—Tarifur R Chowdhury
*Assistant Examiner*—Tara S Pajoohi
(74) *Attorney, Agent, or Firm*—Cantor Colburn LLP; Rosa Suazo

(57) ABSTRACT

A method, apparatus, and computer program product for implementing inspection recipe services are provided. The apparatus includes a test structure including a semiconductor substrate and a number of arrays disposed on the semiconductor substrate. The arrays are linearly arranged and spaced equidistant. Each of the arrays corresponds to a reticle field and includes a number of cells. The test structure also includes a defect programmed into every third array. The defect is programmed in the same location on each third array. The test structure further includes an alignment site defined on the test structure for providing a point of reference upon inspection. The alignment site, in conjunction with a modified reticle pitch extending the distance of one reticle field plus a portion of an adjacent reticle field, are used to perform a random mode inspection of selected arrays in the test structure.

6 Claims, 4 Drawing Sheets

METHOD, APPARATUS, AND COMPUTER PROGRAM PRODUCT FOR OPTIMIZING INSPECTION RECIPES USING PROGRAMMED DEFECTS

BACKGROUND OF THE INVENTION

The present disclosure relates to a method, apparatus, and computer program product for optimizing inspection recipes using a mask with programmed defects.

Determining, optimizing, and monitoring the sensitivity of optical, laser-based, electron-beam and other inspection tools are of great importance for state-of-art semiconductor process technologies. The sensitivity is typically defined by the size of the smallest defect that the inspection can detect.

One approach for optimizing the sensitivity of an inspection tool utilizes an arbitrary production wafer. Initially, an inspection threshold is set to a very low level so that lots of noise is picked up as well as all of the detectable defects based upon the current inspection tool settings. The smallest defect detected may or may not be the smallest defect that exists on the wafer. The inspection may then be optimized by iteratively adjusting the inspection conditions so that the signal of these defects is stronger in order to identify any additional defects. Once optimized, this same production wafer can then be used to monitor the inspection stability by running it again at a later date.

This approach has a number of drawbacks. First, a range of the appropriate sized defects may not exist on every production wafer. As a result, many of these wafers are not good candidates for recipe optimization. If a poor candidate wafer is used, sub-optimal inspections may result. Second, valuable inspection tool time may be consumed evaluating whether a wafer is a good candidate. Finally, each wafer has a finite life for inspection recipe monitoring, making long term monitoring difficult.

One technique for addressing this problem is to utilize programmed defects; that is, intentional defects embedded into the design of a product-like test structure. In a good design, the programmed defects will span the range of interest. Because they are part of the design, they will appear in every reticle field and on every wafer. Therefore, a different wafer can be used every time for long term monitoring.

One disadvantage of this approach is that it is suitable only for array mode inspections, where potential defects are compared to reference sites 2 um to 50 ums away within the same array. Many applications are not suited to array mode inspection and instead require random mode inspection, where the potential defect image is compared to a reference image in the same position on the next die. Logic circuitry is one example where random mode inspection is preferred. Also, for a large area inspection, random mode may be the appropriate choice, since, although some regions within this area have a pattern, no single offset will apply for the entire area. With random mode inspection, however, programmed defects would not be detected because they appear in the same place within each flash field.

One solution to this problem is to utilize two masks for each level of inspection, where the second mask is the same as the first except that it contains the programmed defects. These masks are then alternately flashed across the wafer so that every third reticle field would contain the programmed defects. To differentiate the good die from the bad die, double arbitration may be used. The defective die is compared to its neighbors to the left and right. The main drawback to this approach, however, is that it requires the purchase of an additional reticle per layer of interest which is very expensive. Generating wafers of this type is also expensive in terms of scanner time and only a few wafers would likely be generated.

Another alternative is to place three similar test structures equally spaced across the flash field. One of these structures would contain a programmed defect. Inspection tool sensitivity in random mode could be optimized by using a pitch equal to one third of the reticle field. The disadvantages of this approach are coordination of the reticle layout to get these exact positions in the reticle field and the inspection tool sensitivity is affected by the pitch.

What is needed, therefore, is a cost-effective way to test and optimize sensitivity of inspections tools that leverages the aforementioned benefits of both array mode and random mode inspections.

BRIEF SUMMARY OF THE INVENTION

Embodiments of the invention include an apparatus for implementing inspection recipe optimization services. The apparatus includes a test structure including a semiconductor substrate and a number of arrays disposed on the semiconductor substrate. The arrays are linearly arranged and spaced equidistant. Each of the arrays corresponds to a reticle field and includes a number of cells. The test structure also includes a defect programmed into every third array. The defect is programmed in the same location on each third array. The test structure further includes an alignment site defined on the test structure for providing a point of reference upon inspection. The alignment site, in conjunction with a modified reticle pitch extending the distance of one reticle field plus a portion of an adjacent reticle field, are used to perform a random mode inspection of selected arrays in the test structure.

Additional embodiments include a method for implementing inspection recipe services. The method includes defining a modified reticle pitch for use in inspecting programmed defects on a test structure. The modified reticle pitch extends the distance of one reticle field plus a portion of an adjacent reticle field on the test structure. The test structure includes a number of arrays linearly arranged on the test structure and spaced equidistant. Each of the arrays corresponds to a reticle field and includes a number of cells. The method also includes defining a modified reticle pitch, and using the modified reticle pitch and an alignment site on the test structure to perform a random mode inspection of the test structure.

Further embodiments include a computer program product for implementing inspection recipe services. The computer program product includes instructions for causing a computer to implement a method. The method includes defining a modified reticle pitch for use in inspecting programmed defects on a test structure. The modified reticle pitch extends the distance of one reticle field plus a portion of an adjacent reticle field on the test structure. The test structure includes a number of arrays linearly arranged on the test structure and spaced equidistant. Each of the arrays corresponds to a reticle field and includes a number of cells. The method also includes defining a modified reticle pitch, and using the modified reticle pitch and an alignment site on the test structure to perform a random mode inspection of the test structure.

Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF THE INVENTION

Exemplary embodiments include a method, apparatus and computer program product for optimizing inspection recipe monitoring activities. The apparatus includes a test structure consisting of a series of arrays, which may resemble circuitry in a product chip, e.g., SRAM. The test structure may be a semiconductor substrate. Each array includes a number of cells. Every third array includes one or more programmed defects. The test structure is then tested using a modified reticle field pitch (referred to herein as "stretched reticle field pitch") as the new pitch. In one exemplary embodiment, the stretched reticle field pitch is defined as the reticle field pitch plus an inter-array pitch.

Figure 1:
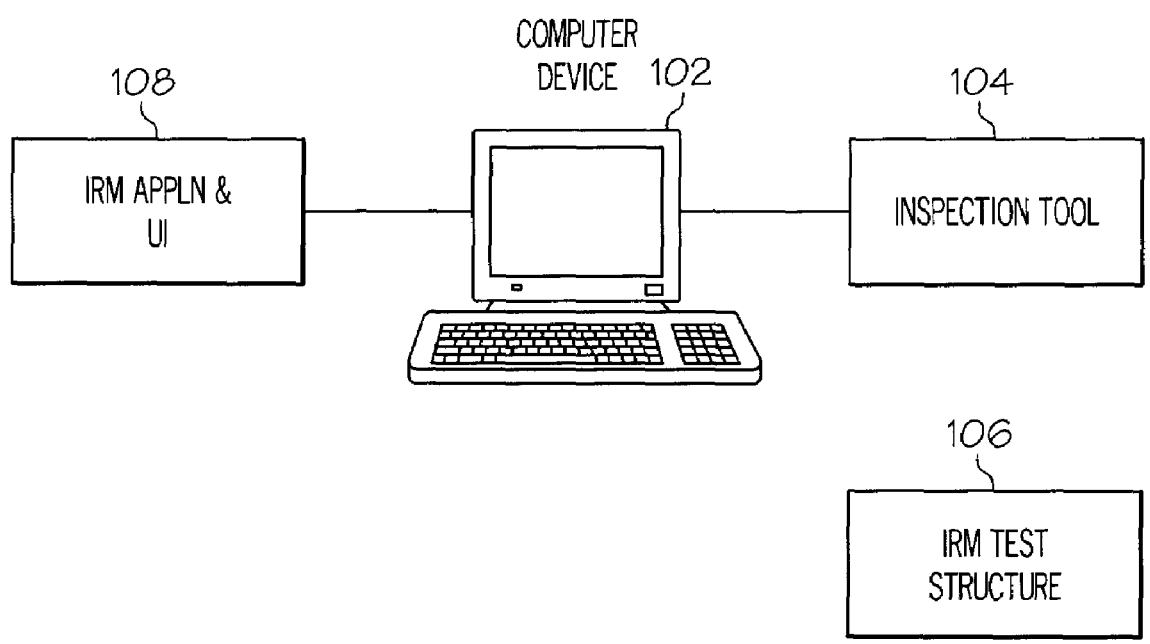
FIG. 1 is a block diagram of a system upon which inspection recipe monitoring activities may be implemented in exemplary embodiments.

Turning now to FIG. 1, a system upon which the inspection recipe monitoring activities may be implemented in exemplary embodiments will now be described. The system of FIG. 1 may be part of a manufacturing facility that produces semiconductor products. The system of FIG. 1 includes a computer device 102 in communication with an inspection tool 104 via any suitable communications technologies (e.g., wireline/wireless, direct communications or via local area network, etc.). Computer device 102 may be implemented by an individual that is tasked with monitoring and optimizing the sensitivity of inspection tool 104. Computer device 102 may comprise any suitable computer processing device, e.g., general-purpose desktop, laptop, etc.

Computer device 102 executes an inspection recipe monitoring application 108 including a user interface for implementing the inspection recipe monitoring activities described herein. A user of computer device 102 may access inspection recipe monitoring application and user interface 108 to define a pitch for a test structure 106, such that the inspection tool 104 scans the test structure using the defined pitch for detecting programmed defects. These activities are described further herein.

Inspection tool 104 may be an optical, laser-based, electron-beam or other similar type of inspection tool that tests production wafers produced within the manufacturing facility of the system of FIG. 1.

Also included in the system of FIG. 1 is an exemplary test structure 106 that is used in implementing the inspection recipe monitoring activities described herein. Test structure 106 may be a simulated production wafer used in semiconductor manufacturing or similar industry. Test structure 106 is scanned via inspection tool 104 for determining and optimizing the sensitivity of the inspection tool 104, such that inspection tool 104 is capable of detecting the smallest possible defects on production wafers generated in the manufacturing facility. Test structure 106 is described further herein.

Figure 2:
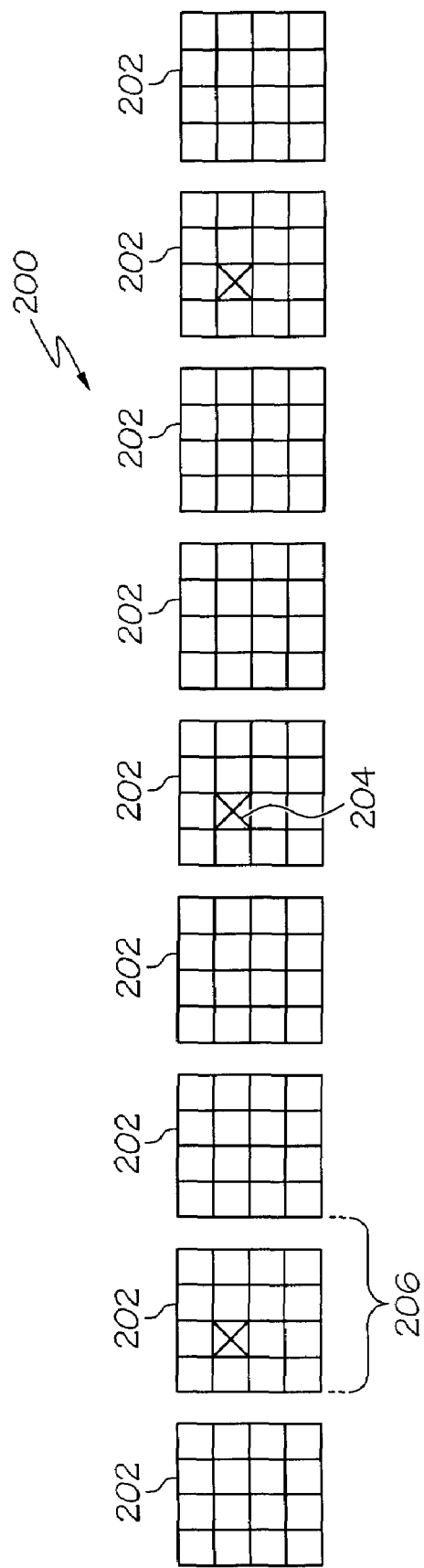
FIG. 2 is a diagram of a sample array pattern that may be used in implementing the inspection recipe monitoring activities in exemplary embodiments.

Turning now to FIG. 2, a sample array pattern that may be used in implementing the inspection recipe monitoring activities will now be described in accordance with exemplary embodiments. The array pattern 200 of FIG. 2 represents a building block for the test structure 106 and includes a number of arrays 202, which collectively mimic a pattern that may be seen in a product chip. Each array 202 contains a number of cells that reflect the overall circuitry pattern designed for the product chip under manufacture. In exemplary embodiments, each array 202 is large enough to set up an inspection area but not so large as to waste reticle field space (e.g., 30 um by 90 um).

As shown in the array pattern of FIG. 2, every third array 202 has been programmed (embedded) with multiple programmed defects (204). In FIG. 2, only one is shown to illustrate the concept. The defects 204 may consist of any type of known defect, e.g., horizontal/vertical opens, horizontal/vertical shorts, and with varying dimensions. As shown in the array pattern 200 of FIG. 2, arrays 202 are horizontally aligned and with equal spacing between them. Each of the arrays 202 has the same size and the same number of cells; that is, the arrays 202 are identical to one another with the exception of the programmed defect. Because the arrays 202 are of equal size and with equal spacing, the pitch between arrays (e.g., inter-array pitch 206) is identical. The inter-array pitch 206 may be defined as the width of an array 202 plus the distance between two neighboring arrays 202. As indicated above, the programmed defects may consist of various opens and shorts and might span a range from better than the targeted inspection tool's sensitivity to well within its range. In addition, programmed defects may be placed at multiple mask levels for the test structure 106 in order to most effectively utilize the structure area and also to test sensitivity to prior level defects.

Figure 3:
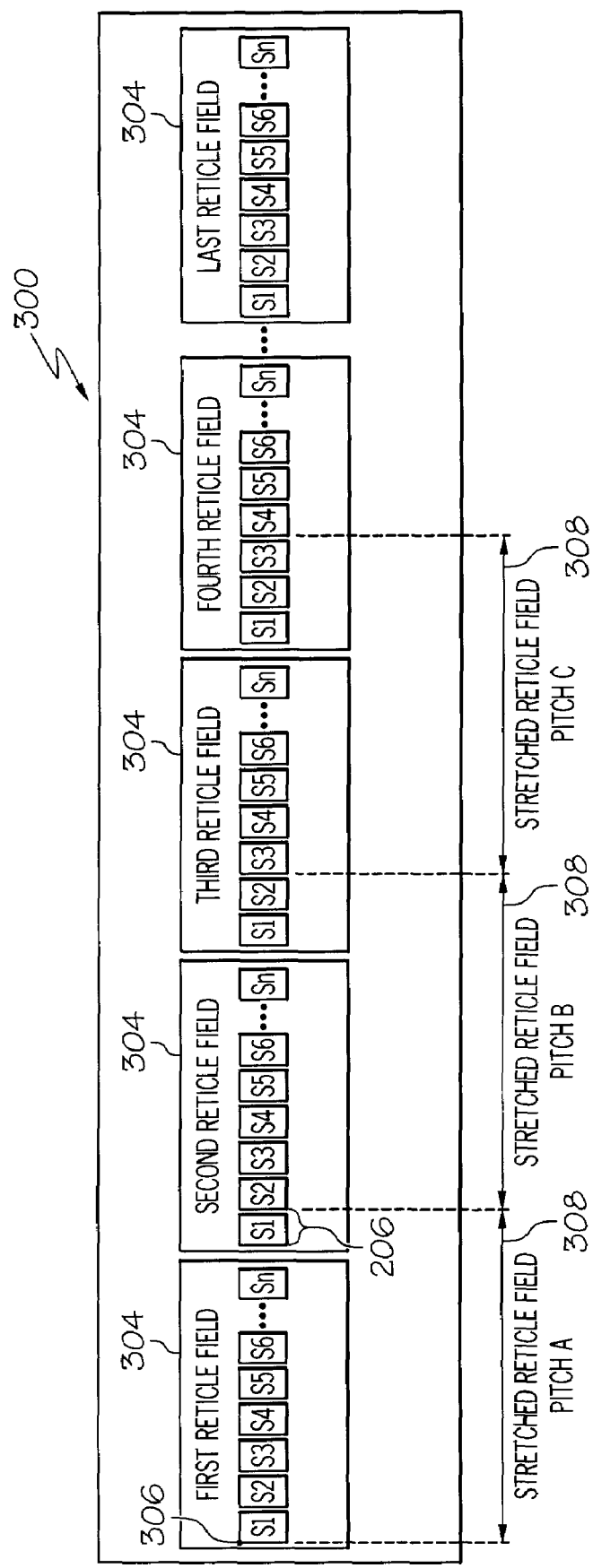
FIG. 3 is an exemplary test structure for use in implementing the inspection recipe monitoring activities in exemplary embodiments.

In exemplary embodiments, the number of array patterns 200 should be equal to or greater than the number of reticle fields spanning the test structure 106. Turning now to FIG. 3, an exemplary wafer schematic 300 will now be described. The wafer schematic 300 of FIG. 3 includes a number of reticle fields 304 (corresponding to the test structure 106 of FIG. 1). Each reticle field 304 contains a test structure comprising an array pattern 200, which in turn, contains a number of arrays 202 (S1, S2, S3 ... Sn). As indicated above, every third array contains one or more programmed defects. Thus, using the example array pattern 200 of FIG. 2, array S2, S5, and S8 in reticle fields 304 in wafer schematic 300 would contain the programmed defect. In addition, an alignment site 306 may be established on the test structure 300 via the array pattern 200 as a point of reference for the inspection tool 104 when setting up an inspection.

The test structure may be manufactured in a sequence of semiconductor manufacturing steps. The array pattern 200 for the test structure, along with other test structures and product chips, may be incorporated into the reticles for each layer in the process sequence. The array pattern 200 on each reticle field 304 may be created on the semiconductor wafer surface according to the process flow. Each reticle field pattern 200 may be tiled across the wafer surface and aligned with the previous patterns on the wafer.

After each reticle field pattern 200 is created across the wafer surface, the inspection recipe monitoring application 108 and user interface may be accessed for initiating an inspection of the test structure 106 by inspection tool 104. As indicated above, the inspection recipe monitoring activities include defining a pitch that is used by the inspection tool in scanning the test structure 106 for programmed defects. In exemplary embodiments, the new pitch is defined as the reticle field pitch (i.e., the width of the reticle field 304 plus the distance between two neighboring reticle fields) plus the inter-array pitch (e.g., inter-array pitch 206 of FIG. 2). This new pitch is referred to herein as a stretched reticle field pitch and is shown in FIG. 3 as stretched reticle field pitch 308.

Figure 4:
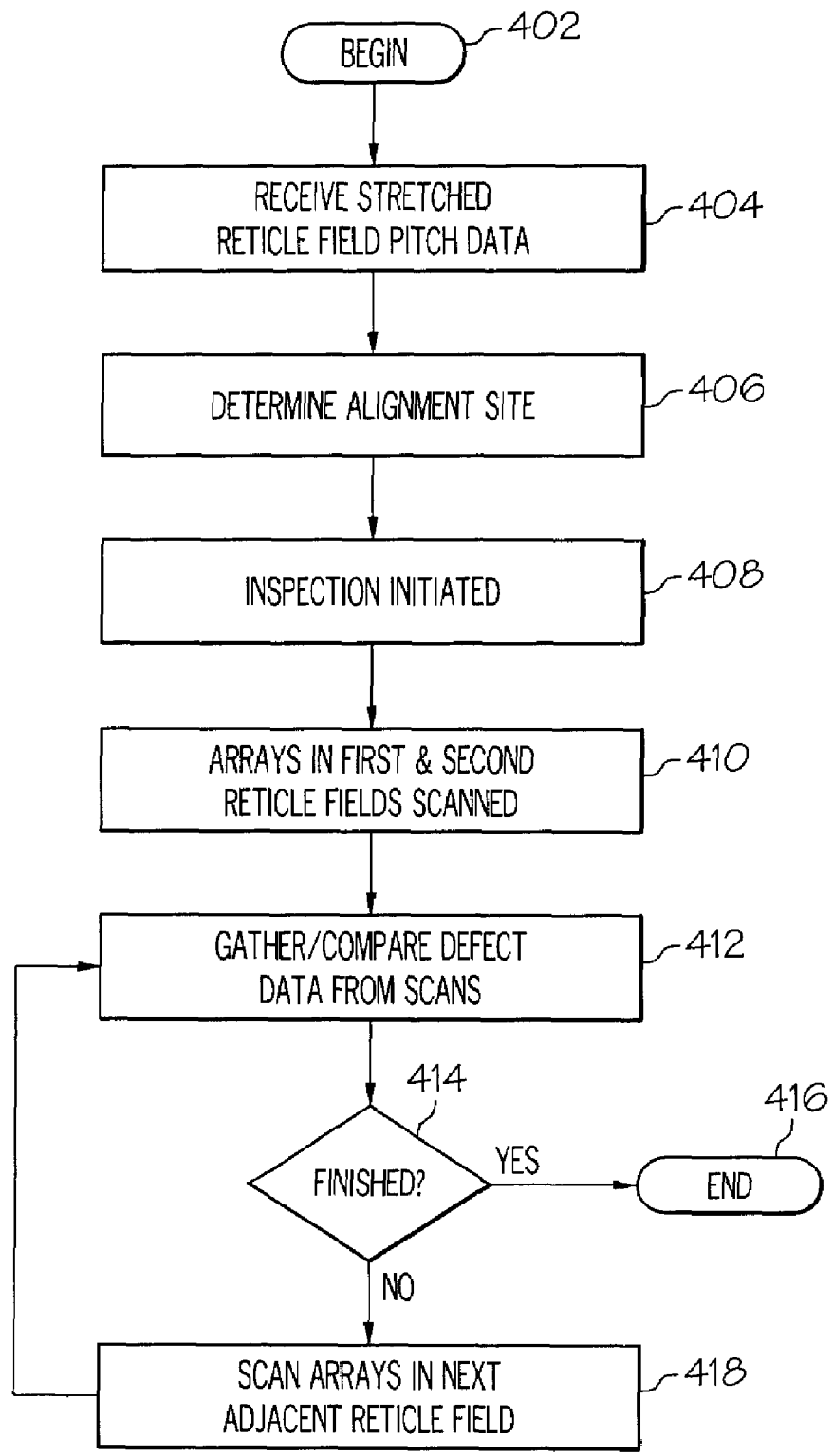
FIG. 4 is a flow diagram describing a process for implementing the recipe monitoring activities in exemplary embodiments.

Turning now to FIG. 4, a flow diagram describing a process for implementing the inspection recipe monitoring activities will now be described in exemplary embodiments. The process begins at step 402 whereby a stretched reticle field pitch is received by the inspection recipe monitoring application 108 at step 404. The inspection recipe monitoring application 108 then identifies an alignment site 306 on the test structure 300 via the inspection tool 104 and the inspection is initiated by inspection tool 104 at step 408.

At step 410, the arrays (S1, S2, S3, . . . Sn) corresponding to the first reticle field 304 and arrays (S2, S3, S4, . . . Sn+1) corresponding to the second reticle field 304 are scanned by the inspection tool 104. The comparison of the scanned arrays spans the stretched reticle field pitches. The data resulting from the scan is gathered and compared by the inspection recipe monitoring application 108 via inspection tool 104 at step 412. For example, array S1 in the first reticle field 304 is compared to array S2 in the second reticle field 304 and so on. Any differences that exist are recorded by the monitoring application 108 as defects. Previous to recording a difference as a defect, the defective location may also be compared to its neighbor on the right.

At step 414, it is determined whether the inspection tool 104 has completed its scan of all reticle fields 304 provided on the wafer. If so, the process ends at step 416. Otherwise, the next reticle field is 304 is scanned and compared to its neighbors using stretched reticle field pitch 308. Array Sn is compared to array Sn−1 on the left and array Sn+1 on the right.

As described above, embodiments can be embodied in the form of computer-implemented processes and apparatuses for practicing those processes. In exemplary embodiments, the invention is embodied in computer program code executed by one or more network elements. Embodiments include computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Embodiments include computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A test structure for implementing inspection recipe services, comprising:
   a semiconductor substrate;
   a number of arrays disposed on the semiconductor substrate, the arrays linearly arranged and spaced equidistant, each of the arrays corresponding to a reticle field and comprising a number of cells;
   a defect programmed into every third array, the defect programmed in the same location on each third array; and
   an alignment site defined on the test structure operable for providing a point of reference upon inspection;
   wherein the alignment site, in conjunction with a modified reticle pitch extending the distance of one reticle field plus a portion of an adjacent reticle field, are used to perform a random mode inspection of selected arrays in the test structure.

2. The test structure of claim 1, wherein the arrays comprise of a pattern of logic circuitry.

3. The test structure of claim 1, wherein defects comprise varying dimensions and include at least one of:
   horizontal open;
   horizontal short;
   vertical open; and
   vertical short.

4. The test structure of claim 1, wherein the modified reticle pitch is defined as a reticle field pitch plus an inter-array pitch.

5. The test structure of claim 1, wherein defects are embedded into multiple mask layers of the test structure.

6. The test structure of claim 1, wherein each of the arrays is 30 um by 90 um.

* * * * *